(12) United States Patent
Chiba

(10) Patent No.: US 6,781,689 B2
(45) Date of Patent: Aug. 24, 2004

(54) CONTINUOUS INSPECTION APPARATUS

(75) Inventor: Shigehisa Chiba, Tokyo (JP)

(73) Assignee: Rieckerman (Japan) Ltd., Tokyo (JP)

( * ) Notice: Subject to any disclaimer, the term of this patent is extended or adjusted under 35 U.S.C. 154(b) by 163 days.

(21) Appl. No.: 09/984,622

(22) Filed: Oct. 30, 2001

(65) Prior Publication Data

US 2002/0054287 A1 May 9, 2002

(30) Foreign Application Priority Data

Nov. 1, 2000 (JP) ........................................ 2000-334564

(51) Int. Cl.[7] .......................... G01N 21/00; G01N 21/90
(52) U.S. Cl. .................. 356/240.1; 356/427; 356/239.6
(58) Field of Search ........................ 250/223 B, 223 R; 356/240.1, 241.3, 237.3, 237.4, 237.5, 237.6, 426, 427, 428, 441, 442, 239.4, 239.5, 239.6

(56) References Cited

U.S. PATENT DOCUMENTS

| | | | |
|---|---|---|---|
| 421,256 A | | 2/1890 | Ferguson |
| 3,905,166 A | * | 9/1975 | Kaiser ............................ 52/65 |
| 4,241,256 A | * | 12/1980 | Tagaya et al. .......... 250/223 B |
| 4,455,225 A | * | 6/1984 | Morimoto et al. .......... 209/588 |
| 4,492,475 A | * | 1/1985 | Takahashi ................... 356/427 |
| 5,296,701 A | | 3/1994 | Kirkman et al. ............. 250/223 |
| 5,536,935 A | * | 7/1996 | Klotzsch et al. ........ 250/223 B |
| 6,055,876 A | * | 5/2000 | Kato ......................... 73/866.5 |
| 6,457,280 B1 | * | 10/2002 | Park .............................. 52/65 |
| 6,473,169 B1 | * | 10/2002 | Dawley et al. .......... 356/239.4 |

FOREIGN PATENT DOCUMENTS

EP  0837311 A1  4/1998

* cited by examiner

*Primary Examiner*—Russell Adams
*Assistant Examiner*—Andrew Sever
(74) *Attorney, Agent, or Firm*—Staas & Halsey LLP

(57) ABSTRACT

A continuous inspection apparatus comprising a central axis placed in a vertical direction, the central axis penetrating a disc-like conveying table which conveys a subject to be inspected, a driving means for driving the conveying table, and a pair of inspection instruments for inspecting the subject to be inspected, one of the inspection instruments being placed at an inside of a circle where a plurality of the subjects are aligned in a circle and another one of the inspection instruments being placed at an outside of the circle, wherein an opening is provided at a place between the central axis and an inner peripheral portion of the conveying table, and a cable extending from one of the inspection instruments is run downward through the opening. According to the apparatus mentioned above, there is no difficulty in movement of the subject to be inspected when the conveying table rotates continuously in a prescribed direction during its operation for inspection and during its operation for verification of accuracy of the apparatus as well.

15 Claims, 4 Drawing Sheets

PRIOR ART

CONTINUOUS INSPECTION APPARATUS

BACKGROUND OF THE INVENTION

1. Field of the Invention

The present invention relates to a continuous inspection apparatus for inspecting a subject to be inspected in a continuous production line without stopping the flow of the subject to be inspected, for example, relates to a continuous inspection apparatus for automatically examining to see whether the subject to be inspected, such as an ample, a vial or the like which contains liquid, is acceptable or not.

2. Prior Art of the Invention

Conventionally, as a continuous apparatus of this kinds, there is known an inspection apparatus for examining if liquid charged into a transparent container contain foreign materials or not, by taking a photograph of the subject by making the subject to be inspected pass in front of a camera to allow the camera to take a photograph of the subject with making light pass through the transparent container as the subject, and then processing the photograph by using an image, processing device.

In order to meet a requirement to increase inspecting speed of the subject, such an inspection system where both a floodlight and a camera follow the subject so as to realize a condition that the floodlight, the camera and the subject are aligned in a straight line for a while, to thereby be able to take a picture of the subject to be inspected without disturbing the production line, such as stopping the flow of the subject in the production line.

As shown in FIG. 3, one of the actual examples of such a conventional continuous inspection apparatus has a pair of inspection instruments. Inner supporting portion 51 and outer supporting portion 52 are disposed to be turntable around a rotation center of conveying table 50 and also are disposed in such a way as to sandwich ring-like conveying table 50 which turns in one direction. Camera 53 is mounted on inner supporting portion 51, and floodlight 54 is mounted on outer supporting portion 52.

Subject to be inspected 57, which is taken onto conveying table 50 from supplying line 56, passes through a place between floodlight 54 and camera 53 when conveying table 50 turns, and then subject to be inspected 57 is discharged into a carrying out line. During a time when subject to be inspected 57 is placed on conveying table 50, moving speed of floodlight 54 and camera 53 is adjusted to a speed corresponding to the moving speed of subject 57 in a prescribed (certain) period of time. With taking a photograph being completed during the prescribed period of time, inspection for detecting foreign materials in the liquid is enabled to be finished during the time subject to be inspected 57 is conveyed.

Next, as is shown in FIG. 4, an upper portion of subject 57 is supported by holding cap 59 so as for subject 57 to be conveyed in a stable position or attitude thereof. Holding cap 59 is mounted on subject 57 during all the time from an in-taking stage where subject 57 is taken onto conveying table 50 to a discharging stage where subject 57 is discharged from conveying table 50. And there is a necessity of providing mechanical operation portion 60 for attaching holding cap 59 to subject 57 when subject 57 is taken onto conveying table 50, and for detaching holding cap 59 from the subject 57 when the subject 57 is moved out from conveying table 50. There is also a need to provide upper table 61 in order to support mechanical operation portion 60.

And upper table 61 is required to be positioned at a prescribed height and to be rotated together with subject 57. Considering convenience of taking photograph, it is undesirable to provide a pole or a wall for supporting upper table 61 between floodlight 54 and camera 53. Therefore, as shown in FIG. 4, ceiling 62 is provided over upper table 61 in order to suspend upper table 61 from ceiling 62.

Furthermore, ceiling 62 is supported, by gate-like frame 65 having enough rigidity and extending from body portion 64 of continuous inspection apparatus 63.

From the condition mentioned above, conventional continuous inspection apparatus 63, which has a structure to suspend upper table 61 from ceiling 62, is required to provide gate-like frame 65 having high rigidity rigid enough for supporting upper table 61 and a driving portion (not shown) for driving upper table 61 in order to secure a precise location of upper table 61, so that the apparatus tends to become large in size, and processing of parts of the apparatus and assembling of the apparatus take a lot of time and the production cost of the apparatus also becomes high.

SUMMARY OF THE INVENTION

An object of the present invention is to eliminate these shortages residing in the conventional continuous inspection apparatus. More precisely, an object of the present invention is to provide a continuous inspection apparatus having a cable attached to a camera, which runs through an opening (aperture or hole or clearance) in a center portion of a conveying table so as to eliminate inconvenience that hampers movements of the subject to be inspected in continuous rotation of the conveying table at a time of verification of the continuous inspection apparatus. Another object of the present invention is to provide a low manufacturing-cost continuous inspection apparatus with an upper table having accuracy in its rotational movement without adopting gate-like frame structure having high rigidity.

A feature of the continuous inspection apparatus of the present invention is that the apparatus comprises a central axis placed in a vertical direction, the central axis penetrating a disc-like conveying table which conveys a subject to be inspected, a driving means for driving the conveying table, and a pair of inspection instruments for inspecting the subject to be inspected, one of the inspection instruments being placed at an inside of a circle where a plurality of the subjects are aligned in a circle and another one of the inspection instruments being placed at an outside of the circle, wherein an opening is provided at a place between the central axis and an inner peripheral portion of the conveying table, and a cable extending from one of the inspection instruments is running downward through the opening.

According to the feature of the apparatus mentioned above, there is no difficulty in movement of the subject to be inspected when the conveying table rotates continuously in a prescribed direction during its operation for inspection and during its operation for verification of accuracy of the apparatus as well.

Another feature of the continuous inspection apparatus of the present invention is that the driving means in the apparatus mentioned above has a gear mechanism for transmitting a rotational driving force of the central axis to the conveying table.

According to the feature of the apparatus mentioned above all mechanism in the driving system driven by both the conveying table and the central axis is driven synchronizedly. Thereby stable operation of the continuous inspection apparatus can be ensured.

Still another feature of the continuous inspection apparatus of the present invention is that the apparatus further comprises, in addition to the features of the apparatus mentioned above, an upper table fixed to the central axis, and a holding cap for holding an upper portion of the subject to be inspected being attached to be vertically movable to the upper table, and the upper table being driven to rotate synchronizedly with the conveying table.

According to the feature of the apparatus mentioned above, without adopting a gate-like frame having high rigidity, the upper table can exert rotational movement with high precision, and inspection can be carried out with high accuracy, to thereby be able to provide a low manufacturing cost continuous inspection apparatus.

The nature and further characteristic features of the present invention will be made more clear from the following descriptions made with reference to the accompanying drawings.

BRIEF DESCRIPTION OF THE DRAWINGS

In the accompanying drawings.

DETAILED DESCRIPTION

Preferred embodiments of the present invention will be described hereunder with reference to the accompanying drawings.

Further, it is first to be noted that the terms showing directions or positions such as "upper", "lower", "right", "left" or the like used herein are represented in an installed state for use or illustrated state in Figs.

The embodiment of the present invention will be described hereunder with reference to FIG. 1 and FIG. 2.

Figure 1:
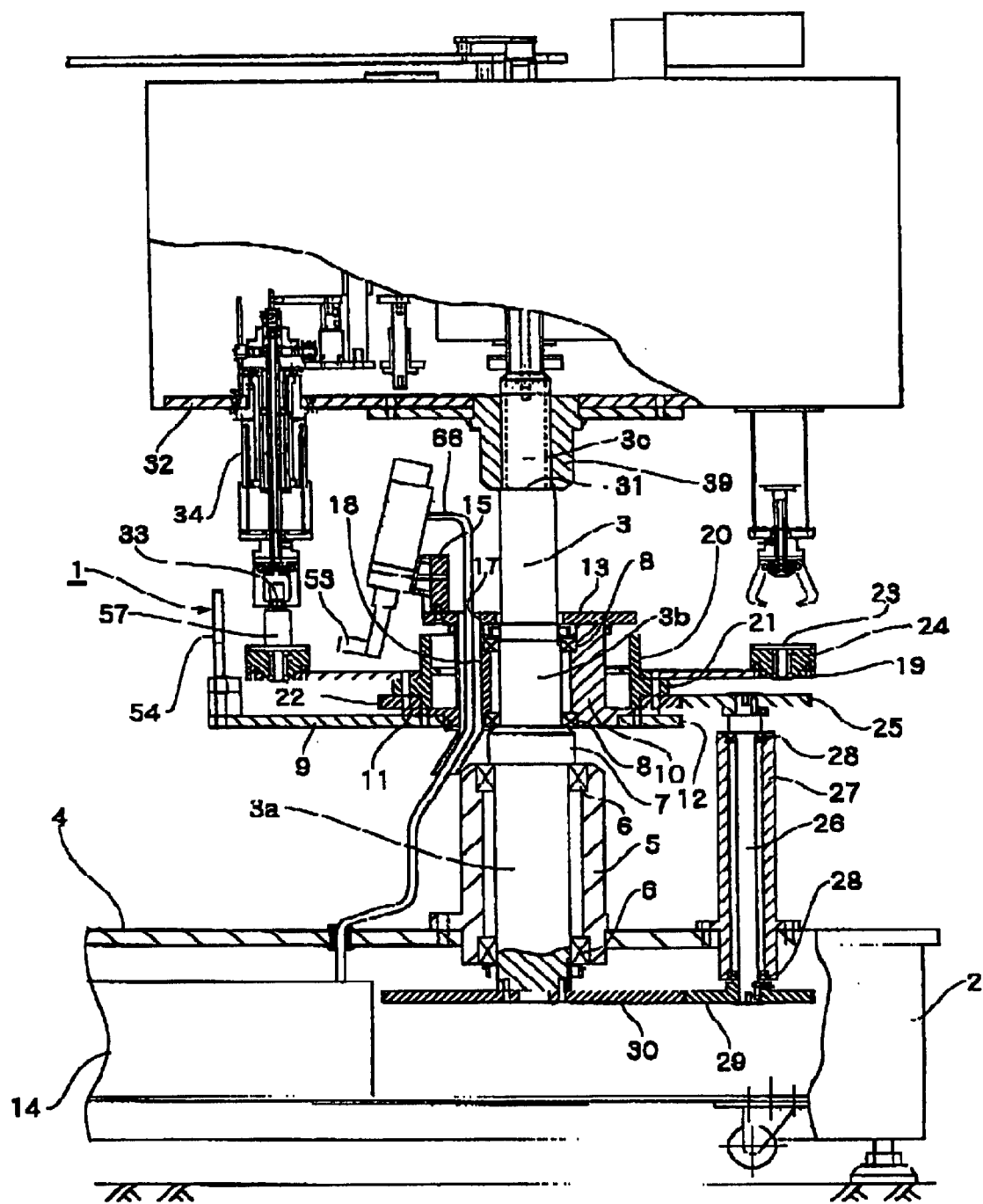
FIG. 1 is a cross sectional view of an essential portion of a continuous inspection apparatus of the present intention.

FIG. 1 is a cross sectional view of an essential portion of a continuous inspection apparatus of the present invention. FIG. 2 is a plan view of an essential portion of the continuous inspection apparatus of the present invention and an upper portion above the upper table is omitted.

A central axial member 3, also referred to as central axis 3, can rotate around a shaft center of the central axis 3, and is provided at an approximately central portion in plan view of body portion 2 of the continuous inspection apparatus 1, and set to stand with a vertical position or attitude. More specifically, vertical type main bearing 5 is fixed to an upper surface of upper base plate 4 of body portion 2 of continuous inspection apparatus 1. Lower portion 3a of central axis 3 is su ported by vertical-type main bearing 5. Larger radius bearings 6, 6 are provided respectively o a radially-inner and longitudinally-upper portion and a radially-inner and longitudinally-lower p ion of vertical-type main bearing 5. Lower portion 3a of central axis 3 is supported to be rotatable by larger radius bearings 6, 6.

Collar portion 7 having an outer diameter larger than that of lower portion 3a of central axis 3 is positioned on an upper end of vertical main bearing 5. Vertical main bearing 5 bears up weight applied on central axis 3. Middle portion 3b having an outer diameter slightly smaller than that of lower portion 3a of central axis 3 is formed on an upper end of collar portion 7.

A pair of middle radius bearings 8, 8 disposed at a prescribed distance from each other are provided on middle portion 3b of central axis 3. A swing-table rotating axial member 10, also referred to as a swing-table rotating axis 10 is positioned around a rotating center of central axis 3 to be rotatable through middle radius bearings 8, 8. Swing table 9 having fan-shape in plan view is fixed to swing-table rotating axis 10.

Mounting seat 11 having an outer diameter larger than that of a body portion of rotating axis 10 is formed on a lower surface of swing-table rotating axis 10. Swing-table 9 having fan shape in plan view and swing-table driving gear 12 are fixed to mounting seat 11. And swing table 9 and swing-table driving gear 12 are disposed symmetrically in relation to a rotation center of swing-table rotating axis 10 (as shown in FIG. 2).

On the other hand, inspection instrument mounting member 13 having approximately disk-like is fixed on the top surface of swing-table rotating axis 10. Camera fixing bracket 15 for fixing camera 53 is fixed on an outer peripheral portion of inspection instrument mounting member 13. Opening (aperture) 17 for making cable 66 of camera 53 get through is provided in an inner peripheral portion of inspection instrument mounting member 13. Penetrating opening (aperture) 18 penetrating vertically is formed, in swing-table rotating axis 10, at a position corresponding to the position of opening 17 which is provided in inspection instrument mounting member 13.

Although, the number of penetrating opening 18 must be at least the same number of opening 17 of inspection instrument mounting member 13, the number of penetrating opening 18 and opening 17 is determined arbitrarily in line with the number of camera 53 or diameter (thickness) of cable 66.

Figure 2:
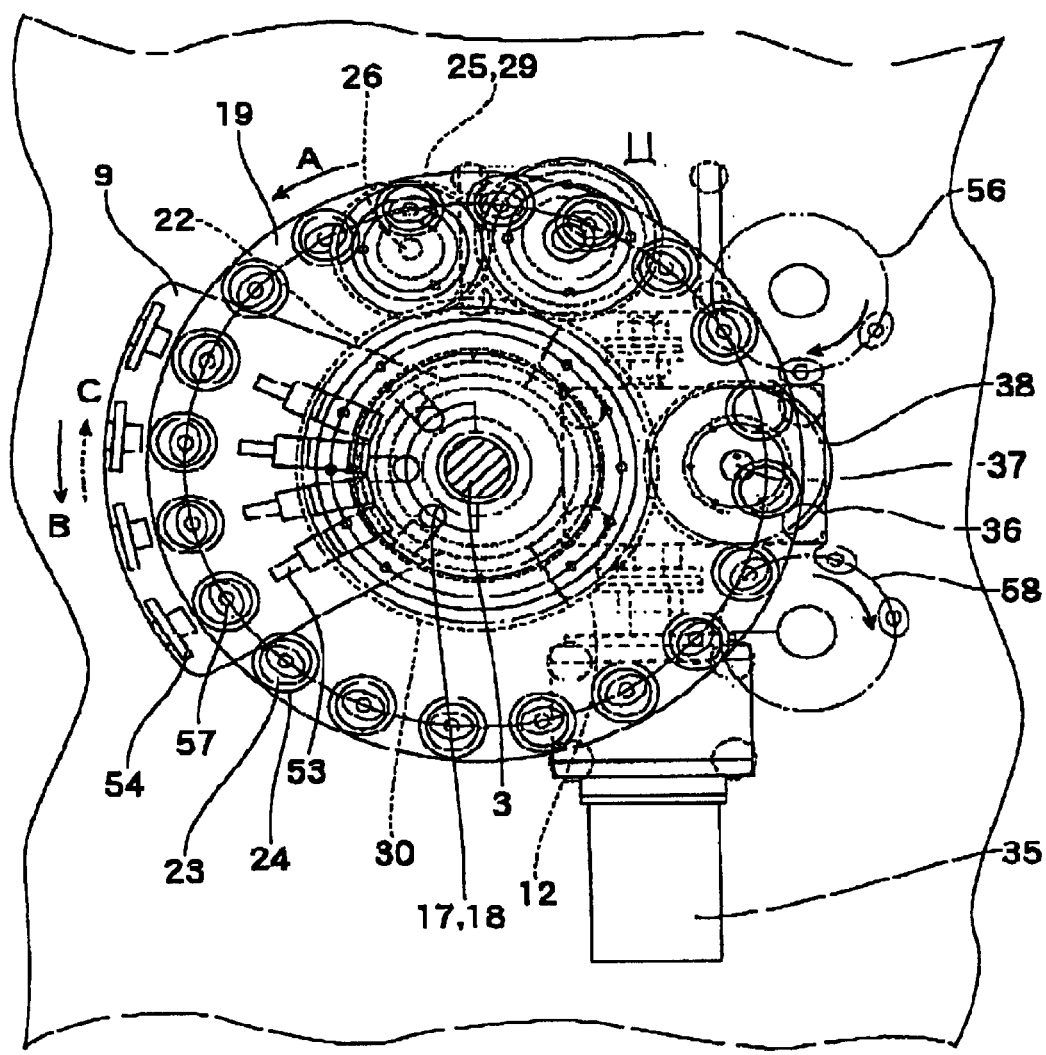
FIG. 2 is a plan view of an essential portion of the continuous inspection apparatus of the present invention, an upper portion over the upper table being omitted.
Figure 3:
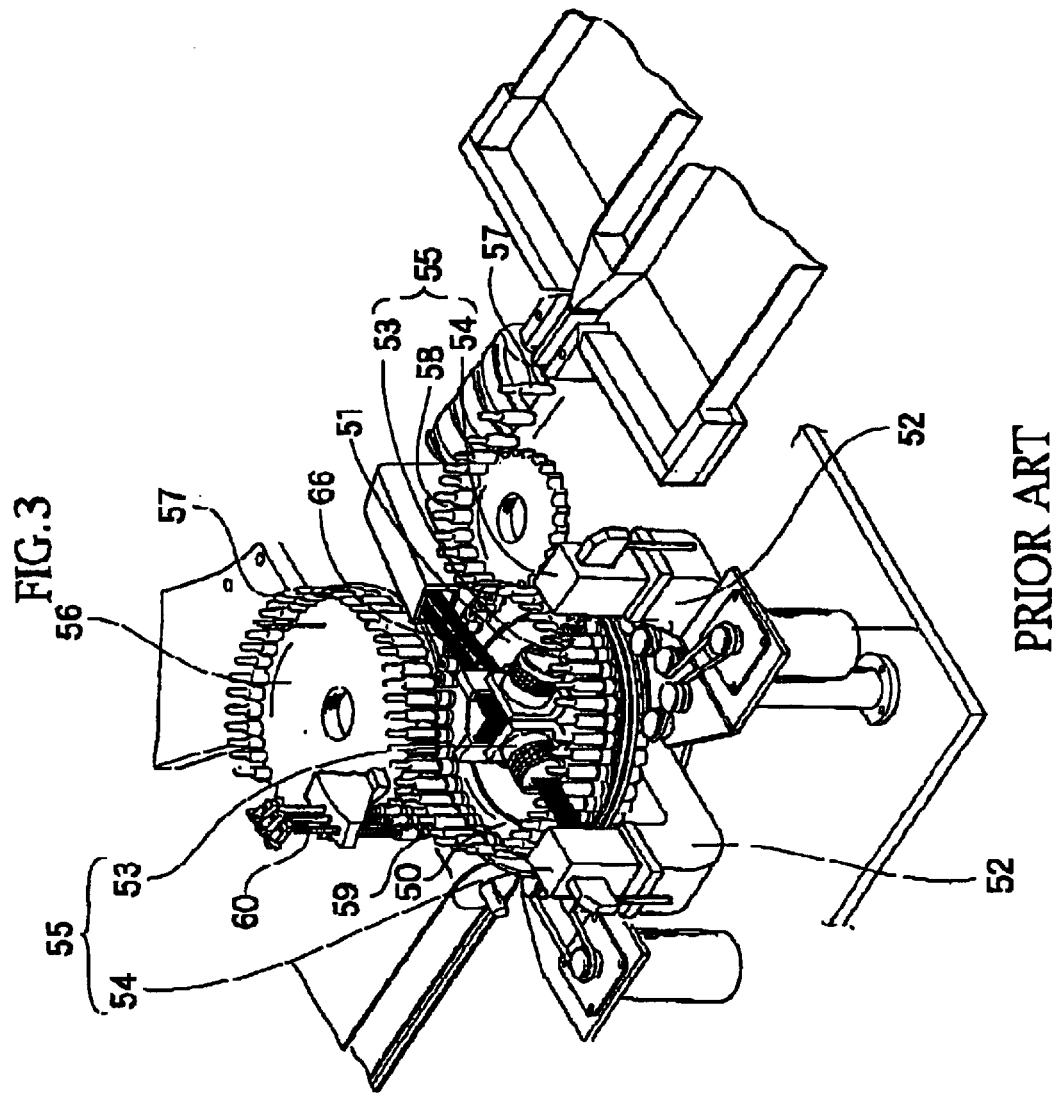
FIG. 3 is a perspective view of an essential portion of a conventional continuous inspection.
Figure 4:
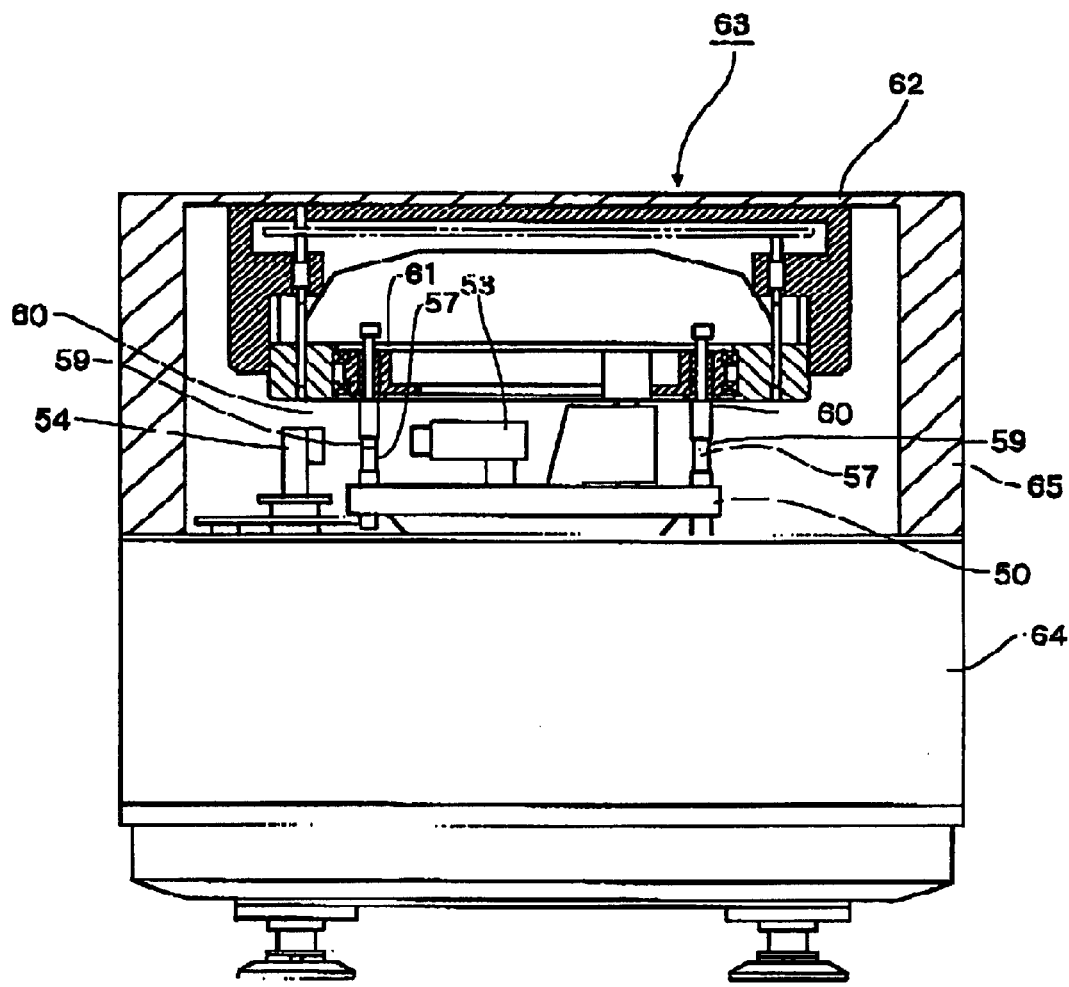
FIG. 4 is a plan view of a portion of the conventional continuous inspection.

In the embodiment shown in FIGS. 1 and 2, 4 sets of camera 53 are attached to inspection instrument mounting member 13 which is fixed to an upper portion of swing-table rotating axis 10. Therefore, 4 sets of floodlight 54 are attached on an outer peripheral portion of swing table 9 in such a fashion that each floodlight 54 is opposed to each camera 53 respectively.

Cable 66 extending from camera 53 is further extending through both opening 17 of inspection instrument mounting member 13 and penetrating opening 18 of swing table rotating axis 10, as mentioned above, and cable 66 is once gotten out of penetrating opening 18 and then connected to image processing device 14 which is accommodated in body portion 2 of continuous inspection instrument 1.

Conveying table rotating axis 20, which is fixed to disk-like shape conveying table 19 for conveying subject to be inspected 57, is attached to an outer peripheral portion of the body portion of swing-table rotating axis 10, to be rotatable around a rotation center of central axis 3 and swing-table rotation axis 10.

Mounting collar portion 21 having an outer diameter smaller than the, diameter of a root circle of swing-table driving gear 12 is formed in a central portion of a longitudinal direction of conveying-table rotating axis 20. Conveying-table driving gear 22 having the same pitch diameter as a pitch diameter of swing-table driving gear 12 is fixed to a bottom source of mounting collar portion 21. And conveying table 19 is fixed to an upper surface of mounting collar portion 21 of conveying-table rotating axis 20.

A plurality of holders 24, 24, 24 ... are provided on an outer peripheral portion of an upper surface of conveying table 19, in an equal pitched fashion with each other for housing rotating plate 23 which is freely rotatable itself. Rotating plate 23 supports a bottom surface of subject to be inspected 57.

Upper small gear 25 engages with conveying-table driving gear 22. Transfer shaft 26 fixed to upper small gear 25 is supported to be rotatable, through small bearings 28, 28, by vertical trailing bearing 27 which is fixed to and set to stand to upper base plate 4 of body portion 2 of continuous inspection apparatus 1. A bottom end portion of transfer shaft 26 protrudes downwardly from a bottom surface of vertical type trailing gear 27, the bottom surface of which is positioned in an inner portion of body portion 2 of continuous inspection apparatus 1, and joins up with lower small gear 29. And the pitch diameter of lower small gear 29 is set to be equal to that of upper small gear 25.

Lower small gear 29 engages with central axis rotating gear 30 which is fixed to a lower end potion of central axis 3. The pitch diameter of central axis rotating gear 30 is set to be equal to that of conveying-table driving gear 22.

Upper portion 3c of central axis 3 is formed on an upper portion of middle portion 3b of central axis 3. The outer diameter of the upper portion is slightly smaller than that of middle portion 3b. Stop portion 31, which is positioned between middle portion 3b and upper portion 3c, is abutted against a lower surface of boss portion 39 of upper table 32, to thereby define a vertical position of upper table 32. Central axis 3 and upper table 32 are fixed to each other so that both central axis 3 and upper table 32 can make the same rotational movement.

Holding-cap put-on and put-off mechanism portion 34, which vertically moves holding cap 33 for holding an upper portion of subject to be inspected 57, is attached to a lower surface of an outer peripheral portion of upper table 32, in such a manner that holding-cap put-on and put-off mechanism portion 34 is positioned at a place opposite to rotating plate 23 in holder 24 which is provided on conveying table 19.

Holding-cap put-on and put-off mechanism portion 34 is made to operate in such a manner that at a time when subject to be inspected 57 is supplied to conveying table 19 from supplying line 56, holding cap 33 comes down to the upper portion of subject 57 and tightly grips the upper portion of the subject 57, and at a time when subject 57 is discharged from conveying table 19 to conveying line 58, holding cap 33 unfastens its grip and goes upward, thereby making subject 57 free from the grip As shown in FIG. 2 which is a plan view of the essential portion of the continuous inspection apparatus of the present invention, rotary index 36 is connected to motor with a reduction gear 35. Thereby, rotational movement of motor 35 is converted into swing-type rotational movement by vertical output axis 37 of rotary index 36. In the present invention, the word of swing-type rotational movement is used as a repetitive movement repeating a right-hand and left-hand rotational movement within a prescribed range of rotational angle, and more specifically, a repetitive movement in such a way that after one way rotation with a prescribed speed from an original position to a prescribed position, another way rotation opposite to the one way rotation occurs, with more faster speed than that of the one way rotation, to the original position from the prescribed position.

Swing gear 38 is fixed to vertical output axis 37 of rotary index 36 and engages with swing-table driving gear 12.

Therefore, swing table 9 makes a swing-type rotational movement within a swinging range that is enlarged in compliance with a gear ratio of both gears 12 and 38.

Next, operations of the continuous inspection apparatus of the present invention will be described hereinafter.

When subject to be inspected 57 is supplied from supplying line 56 to conveying table 20, a lower portion of subject 57 is supported by rotating plate 23 which can rotate itself freely in holder 24. At the same time, holding-cap put-on and put-off mechanism portion 34 begins to operate and holding cap 33 comes down to the upper portion of subject 57 and then tightly grips the upper portion of subject 57. Thereafter, subject 57 is conveyed along with the rotational movement of conveying table 19 under a condition that subject 57 can freely rotate on its own axis, until it reaches to carrying out line 58.

In the embodiment shown in FIGS. 1 and 2, 4 pairs of inspection instruments 55 comprising cameras 53 and floodlights 54 are installed. These 4 pairs of inspection instruments 55 swing rotationally within a prescribed range of rotation angle in line with a swing type rotational movement of swing-table rotating axis 10.

As shown in FIG. 2 which is a plan view of an essential portion of the apparatus of the present invention, when conveying table 19 rotates in an anti-clockwise direction (direction of arrow A), swing-table rotating axis 10 rotates in accordance with the movement of conveying table 19 in a direction (direction of arrow B) within a prescribed range of rotation angle under the control of rotary index 36. And after rotating to the prescribed angle, swing-table rotating axis 10 swings back swiftly (in a direction of arrow C) to the initial position.

During the time the swing-table rotating axis 10 rotates side by side with conveying table 19, subject to be inspected 57 such as an ample or a vial of a transparent container containing liquid is rotated around its axis at a high speed, with the subject 57 being held between rotating plate 23 and holding cap 33, and then putting a brake on rotation to bring subject 57 to a stop quickly, and then detecting images of foreign material, which is floating and rotating together with the liquid, with camera 53 under the condition that the subject 57 is radiated by light from floodlight 54.

When subject 57 is moved out of conveying table 19 toward carrying out line 58 after completion of inspection on conveying table 19, subject to be inspected 57 begins to depart from rotating plate 23 and then moves toward carrying out line 58. At the same time holding cap put on and put-off mechanism portion 34 begins to operate to make holding cap 33 put off from the subject 57 and goes upward, thereby making subject 57 free from holding cap 33.

Cable 66 extending from camera 53 is further extended through both opening 17 of inspection instrument mounting member 13 and penetrating opening 18 of swing-table rotating axis 10, and cable 66 is once gotten out of penetrating opening 18 and then connected to image processing device 14 which is accommodated in body portion 2 of inspection instrument 1. Therefore when the same subject 57 held between conveying table 19 and holding cap 33 is rotated continuously around central axis 3 at a time of verification to confirm accuracy of continuous inspection apparatus 1. Cable 66 of camera 53 does not prevent the movement of subject 57 because cable 66 is housed in penetrating opening (aperture) 18 in swing-table rotating axis 10.

Furthermore, although in the embodiment shown in Figs, camera 53 is placed at an inside of the circle where a plurality of subjects to be inspected 57 is aligned in a circle, and floodlight 54 is placed at an outside of the circle. However, the present invention is not limited thereto. Camera 53 can be placed at an outside of the circle, and the floodlight 54 can be placed at an inside of the circle. In this case a cable of floodlight 54 can be housed in penetrating opening (aperture) 18 in swing-table rotating axis 10, so that the cable does not become a hindrance at the time of accuracy verification of the continuous inspection apparatus 1.

What is claimed is:

1. A continuous inspection apparatus comprising:
   a central axial member positioned in the vertical direction, the central axial member penetrating a disc-like conveying table which conveys a subject to be inspected;
   driving means for driving e conveying table; and
   a pair of inspection instruments inspecting the subject to be inspected, one of the inspection instruments being placed at an inside of a circle where a plurality of the subject are aligned in a circle and another one of the inspection instruments is placed at an outside of the circle,
   wherein a rotating axial member rotates about the central axial member and has an opening provided at a place between the central axial member and an inner peripheral portion of the conveying table, and wherein a cable extends from one of the pair of inspection instruments, and is passed downward through the opening.

2. A continuous inspection apparatus according to claim 1, wherein the driving means has a gear mechanism for transmitting a rotational driving force of the central axial member to the conveying table.

3. A continuous inspection apparatus according to claim 2, further comprising:
   an upper table fixed to the central axial member, and
   a holding cap holding an upper portion of the subject to be inspected, the holding cap being attached to the upper table be vertically movable, and the upper table being driven to rotate synchronously with the conveying table.

4. A continuous inspection apparatus according to claim 1, wherein said conveying table, said central axial member and said rotating axial member rotate independently with respect to each other.

5. A continuous inspection apparatus according to claim 1, wherein said central axial member rotates independently from the rotating axial member.

6. A continuous inspection apparatus comprising:
   a conveying table having an inner peripheral portion conveying a subject to be inspected, a plurality of the subjects to be inspected being aligned in a circled line on the conveying table;
   a central axial member placed in the vertical direction, the central axial member penetrating the conveying table so as to make the conveying table turn around the central axial member;
   a pair of inspection instruments inspecting the subject to be inspected, one of the inspection instruments being positioned at an inside of the circled line of the subjects and another one of the inspection instruments being positioned at an outside of the circled line of the subjects, the pair of inspection instruments being placed opposite to each other across the circled line of the subjects;
   a mounting member mounting the inspection instruments, the mounting member being penetrated by the central axial member so as to make the mounting member turn around the central axial member;
   driving means for driving the conveying table and the mounting member around the central axial member;
   a rotating member rotating about the central axial member and having an opening provided at a place between the central axial member and an inner peripheral portion of the conveying table.

7. A continuous inspection apparatus according to claim 6, wherein the subject to be inspected is a transparent container having an upper portion and a bottom portion.

8. A continuous inspection apparatus according to claim 7, wherein the container contains liquid.

9. A continuous inspection apparatus according to claim 7, further comprising:
   an upper table fixed to the central axial member; and
   a holding cap holding the upper portion of the subject to be inspected, the holding cap being attached to be vertically movable with respect to the upper table, and the upper table being driven to rotate synchronously with the conveying table.

10. A continuous inspection apparatus according to claim 6, wherein the mounting member exerts a swing-type rotational movement.

11. A continuous inspection apparatus according to claim 6, wherein one of the pair of inspection instruments is a camera, and the other of the pair of inspection instruments is a floodlight.

12. A continuous inspection apparatus according to claim 6, wherein the conveying table turn around the central axial member synchronously with the mounting member.

13. A continuous inspection apparatus according to claim 6, wherein the driving means has a gear mechanism for transmitting a rotational driving force of the central axial member to the conveying table.

14. A continuous inspection apparatus comprising:
    a conveying table having an inner peripheral portion conveying a subject to be inspected, a plurality of the subjects to be inspected being aligned in a circled line on the conveying table;
    a central axial member placed in the vertical direction, the central axial member penetrating the conveying table so as to make the conveying table turn around the central axial member;
    a pair of inspection instruments inspecting the subject to be inspected, one of the pair of inspection instruments being positioned at an inside of the circled line of the subjects and another one of the pair of inspection instruments being positioned at an outside of the circled line of the subjects, the pair of inspection instruments being placed opposite to each other across the circled line of the subjects;
    a mounting member mounting one of the inspection instruments, the mounting member being penetrated by the central axial member so as to make the mounting member turn around the central axial member;
    driving means for driving the conveying table and the mounting member around the central axial member;
    a rotating axial-member rotating about the central axial member and having an opening provided at a place between the central axial member and an inner peripheral portion of the conveying table;
    a swing table having a fan shape in plan view being fixed to the mounting member; an upper table being fixed to an upper portion of the central axial member and being moved horizontally; and a holding member holding an upper portion of the subject to be inspected and being attached to a lower surface of the upper table, another one of the pair of inspection members being fixed to an outer peripheral portion of the swing table, exerting a swing-type rotational movement.

15. A continuous inspection apparatus comprising:

a central axial member;

a rotating axial member rotating about the central axial member and having an opening;

a conveying table conveying a subject to be inspected, said conveying table having an opening therein and being coupled to said rotating axial member; and first and second inspection instruments inspecting the subject to be inspected, said first and second instruments being positioned adjacent said conveying table, so as to be on opposite sides of the subject to be inspected, said first inspection instrument having a cable extending therefrom which extends through the opening in said conveying table, and the opening in said rotating axial member.

* * * * *

UNITED STATES PATENT AND TRADEMARK OFFICE
CERTIFICATE OF CORRECTION

PATENT NO. : 6,781,689 B2
DATED : August 24, 2004
INVENTOR(S) : Shigehisa Chiba

It is certified that error appears in the above-identified patent and that said Letters Patent is hereby corrected as shown below:

<u>Title page,</u>
Item [73], Assignee, please change the name to -- Rieckermann --.

<u>Column 7,</u>
Line 17, please delete "e" and insert -- the --.

<u>Column 8,</u>
Line 32, please delete "turn" and insert -- turns --.
Line 67, after ";" please state a new paragraph.

Signed and Sealed this

Fifth Day of April, 2005

JON W. DUDAS
*Director of the United States Patent and Trademark Office*